United States Patent [19]

Smernoff

[11] 4,253,845
[45] Mar. 3, 1981

[54] GAS-LIQUID EQUILIBRATION APPARATUS

[75] Inventor: Ronald B. Smernoff, Belmont, Calif.

[73] Assignee: Analytical Products, Inc., Belmont, Calif.

[21] Appl. No.: 7,768

[22] Filed: Jan. 30, 1979

[51] Int. Cl.³ .................. G01N 33/96; G01N 33/50
[52] U.S. Cl. ............................... 23/230 B; 23/928; 261/82; 261/122; 422/50; 422/99
[58] Field of Search ............... 23/230 B, 928; 422/68, 422/102, 99, 101, 50; 55/68; 261/122, 82, 112; 210/359

[56] References Cited

U.S. PATENT DOCUMENTS 3,973,915   8/1976   Raffaele et al. .................... 422/68
4,057,499   11/1977  Buono ............................... 422/101 X

OTHER PUBLICATIONS

Noonan et al, Clinical Chemistry, vol. 20, No. 6, 1974 pp. 660–665.

*Primary Examiner*—R. E. Serwin
*Attorney, Agent, or Firm*—Phillips, Moore, Weissenberger, Lempio & Majestic

[57] ABSTRACT

Standards solutions and test samples are necessary for blood gas analyzers. Production of such standards and test samples has only been possible with relatively expensive apparatus. Such standards and test samples are provided herein by apparatus 10 which equilibrates a liquid 12 with a gas 14. The apparatus 10 includes a barrel 16 open at a first end 18 and at a second end 20. A piston 22 fits matingly reciprocally within the barrel 16. A flow control 26 allows the gas 14 to flow into the second end 20 of the barrel 16 and prevents the liquid 12 from flowing out of the second end 20 of the barrel 16. The gas 14 is allowed to flow out of the barrel 16 above a liquid level 44 therein. A method utilizing the apparatus 10 to prepare standard and test sample solutions is also set out.

24 Claims, 7 Drawing Figures

GAS-LIQUID EQUILIBRATION APPARATUS

DESCRIPTION

1. Technical Field

This invention relates to an apparatus for quickly and inexpensively equilibrating a sample of liquid with a gas. Such apparatus is particularly useful for preparing standard and test solutions for calibrating blood gas analysis instruments.

2. Background Art

There are a number of equilibrators known for preparing a calibration standard and one or more test samples for a blood gas analyzer. In one such apparatus, the sample or standard is prepared by blowing gas onto the surface of a solution held in a tube or other type of cell, while the solution is being oscillated or spun to increase the gas-liquid contact area. Such an apparatus is relatively complicated and expensive, requiring means for accomplishing the spinning, among other things. Also, a relatively long time is required to accomplish equilibration, since even with spinning, the available surface area for absorption of the gas is relatively small. Thus, each standard or test sample generally requires from 20–30 minutes to equilibrate. Further, it is customary to prepare one standard and two test samples in each 8 hour shift, thus leading to a down time of 1 to 1½ hours per shift for preparing samples for the calibration of a blood gas analyzer and for the testing thereof.

Another prior art gas-liquid equilibrator will produce samples in a much shorter period of time by bubbling gas into a cell below the surface of the liquid being equilibrated therewith. The cell itself is generally of a polymeric material and is matingly held within a cavity in a block of copper or other heat conductive metal. Equilibration time is fast and more than one standard or test sample can be produced simultaneously through providing a plurality of bores in the copper block and a plurality of gas lines for delivering gas, one for delivering gas beneath the surface of each of the solutions in each of the cells. While an apparatus as just described has significant advantages over other prior art apparatus, the cost thereof is relatively high. That is, the apparatus requires a machined block of metal, or the like, proper maintenance of the temperature thereof, proper gas-solid phase equilibration of the temperature of the gas with the temperature of the block, etc. Also, the solutions prepared in the cells of such an apparatus must be capped and transferred elsewhere by pouring or by being sucked up into a syringe or the like. While this can be readily carried out by a trained technician, it does introduce a possibility for operator error.

DISCLOSURE OF INVENTION

The present invention is directed to overcoming one or more of the problems as set forth above.

According to the present invention, an improvement is provided in a syringe apparatus which has a piston reciprocally matingly fitting within a barrel. The improvement comprises flow control means for allowing a gas to flow into a downfacing end of the barrel and for preventing flow of a liquid out of the downfacing end of the barrel. Means are also provided for allowing the gas to flow out of the barrel above a level of the liquid held therein.

Also, according to the present invention, a method is provided of equilibrating a gas with a liquid which fills a generally vertical barrel up to a liquid level therein, the barrel having a piston reciprocally matingly fitting therein and having means for allowing the gas to flow thereoutof above the liquid level therein. The method comprises flowing the gas upwardly through the liquid from an originally generally downwardly facing end of the barrel while preventing the liquid from flowing downwardly out of the barrel until a desired degree of equilibration has been obtained. The gas flowing is halted while the liquid flow preventing is continued. The gas flow allowing means is blocked off, the barrel is inverted, and the liquid flow preventing is stopped. The piston is then advanced sufficiently to expel any remaining gas from between the piston and the originally generally downwardly facing and now generally upwardly facing end of the barrel.

It is desirable to have an inexpensive and easy to use apparatus wherein a liquid can be equilibrated with a gas. It is also desirable that the apparatus be such that the liquid is in a proper container for use as a standard or test sample for insertion into a blood gas analyzer without any intermediate transfer step. And, it is desirable that the above be accomplishable in a relatively short period of time, whereby standard and test sample solutions can be prepared without excessive down time.

BRIEF DESCRIPTION OF DRAWING

The invention will be better understood by reference to the figures of the drawings, wherein like numbers denote like parts throughout, and wherein.

BEST MODE FOR CARRYING OUT THE INVENTION

Figure 1:
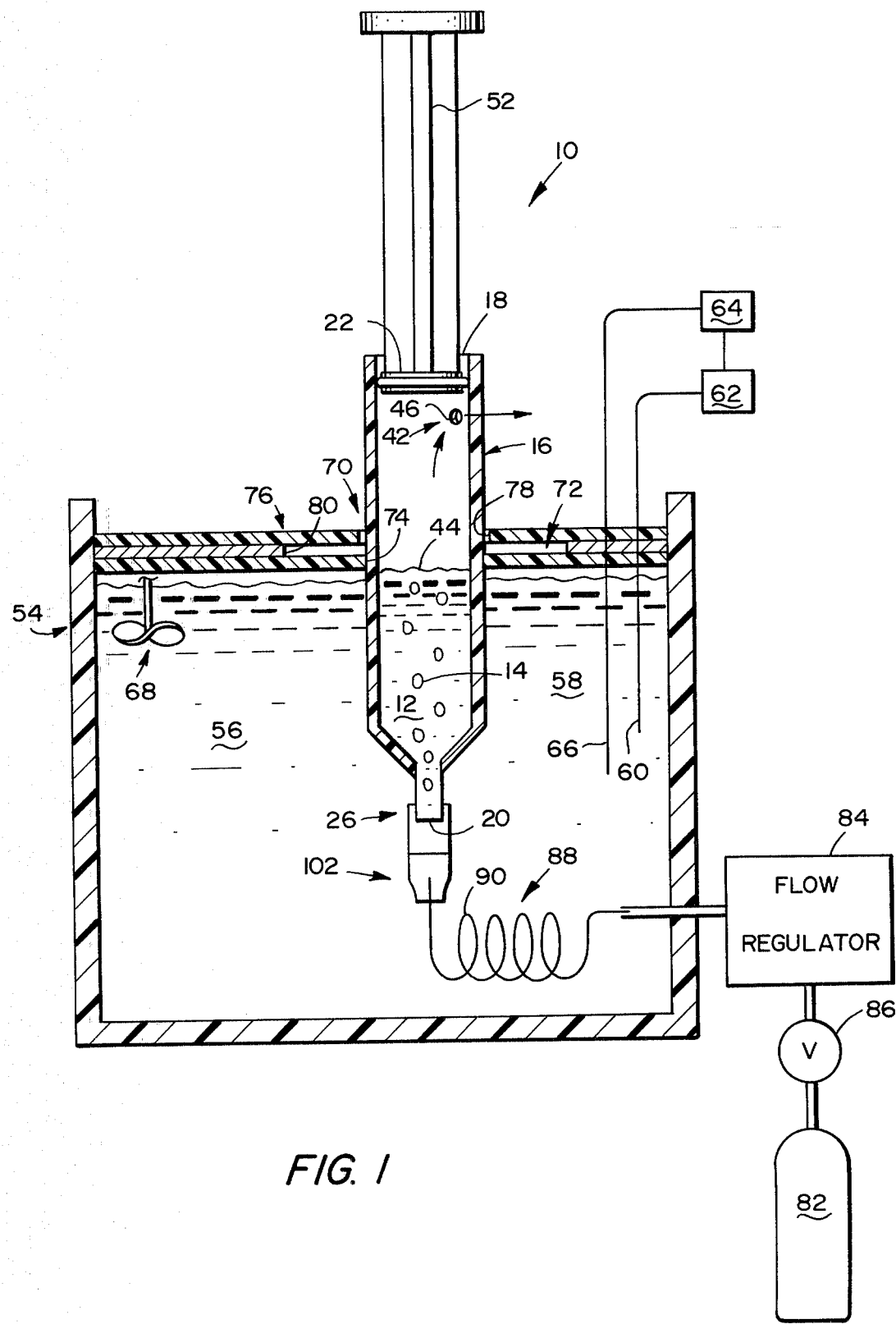
FIG. 1 illustrates, in side view, partially in section and partially schematically, an improvement in accordance with an embodiment of the present invention.

Adverting first primarily to FIG. 1, there is illustrated therein an apparatus 10 in accordance with the present invention. The apparatus 10 serves for equilibrating a liquid 12 with a gas 14.

Figure 3:
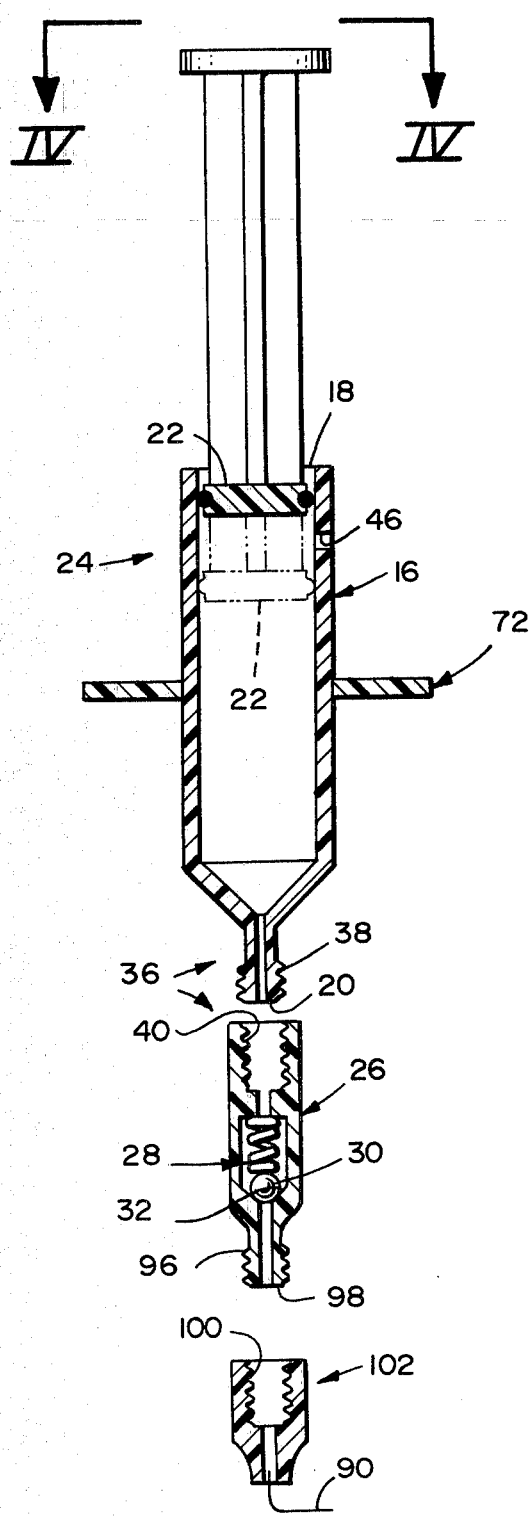
FIG. 3 illustrates, in exploded side-sectional view, details of an improvement in accordance with an embodiment of the present invention.

Adverting particularly to FIGS. 1 and 3, it will be seen that the apparatus 10 includes a barrel 16 which is open at a first end 18 thereof and also open at a second end 20 thereof. A piston 22 is in mating slidable reciprocal relation within the barrel 16. In essence, then, it is clear that the apparatus 10 comprises a conventional syringe 24 which comprises the piston 22 which reciprocally matingly fits within the barrel 16. The present invention modifies this conventional syringe 24 in a manner which makes it suitable for equilibrating the liquid 12 with the gas 14, and for delivering a thus equilibrated sample of the liquid 12 to a blood gas analyzer with minimum chance of any contamination thereof.

In accordance with the present invention, flow control means 26 are provided which allow the gas 14 to flow into the second end 20 of the barrel 16 and which also serve for preventing flow of the liquid 12 out of the second end 20 of the barrel 16. As will be clear by reference to FIG. 3, the flow control means 26 shown therein comprises a check valve 28 which is made up of a ball 30 which fits against a seat 32. In a conventional manner, downward flow is prevented by the ball 30 sitting upon the seat 32. However, upward flow is possible, since the ball 30 then lifts off of the seat 32 due to the positive pressure from below.

Figures 5, 7:
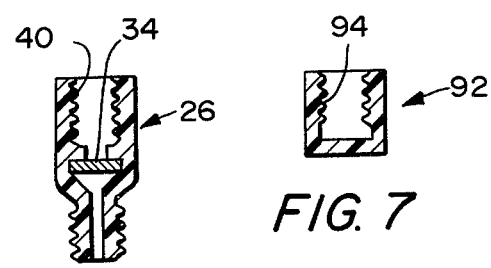
FIG. 5 illustrates, in side-sectional view, an improvement in accordance with an alternate embodiment of the present invention.
FIG. 7 illustrates in side-sectional view, auxiliary apparatus useful with an embodiment of the present invention.

Adverting briefly to FIG. 5, it will be noted that alternate flow control means 26 are illustrated therein, in particular, a membrane 34 is illustrated which is impervious to flow of the liquid 12 and is pervious to flow of the gas 14. Generally, the membrane 34 will have microscopic (capillary) paths therethrough, and the surface of the membrane 34 will be hydrophobic so that the liquid 12 will not web the microscopic capillary paths, and thus will be held from flowing downwardly therethrough. On the other hand, the gas 14 will not be held up significantly by the microscopic or capillary paths and will simply pass upwardly therethrough against the head created by the liquid 12. Equilibration can take place in such an apparatus in not more than 3 to 4 minutes for a 10 cc. sample of an aqueous liquid 12.

Whether the flow control means 26 of FIG. 3 or that of FIG. 5 is utilized, there will generally be provided means 36 for removably securing the flow control means 26 to the second end 20 of the barrel 16. Such removable securing means 36 will normally comprise screw threads 38 on the second end 20 of the barrel 16 which mate with screw threads 40 on the flow control means 26. This allows disengagement of the barrel 16 from the flow control means 26, which disengagement is desirable for allowing expulsion of excess gas 14, so that the barrel 16 is fully filled with the liquid 12 below the piston 22, after equilibration thereof with the gas 14. The liquid 12 is thereby made ready for use in a blood gas analyzer, as will be pointed out in more detail in following.

Adverting again to FIGS. 1 and 3, it will be noted that means 42 are provided for allowing the gas 14 to flow out of the barrel 16 above a liquid level 44 therein. In the embodiment illustrated in FIGS. 1 and 3, the gas flow allowing means 42 simply comprises a hole 46 through the barrel 16 intermediate the liquid level 44 and the first end 18 thereof. The hole 46 is positioned a spaced distance away from the end 18 of the barrel 16 to allow the piston 22 to move close enough to the first end 18 of the barrel of 16 to allow the gas 14 to flow out of the hole 46. Both FIG. 1 and FIG. 3 illustrate the piston 22 in this retracted position. It should also be noted that if the piston 22 is moved downwardly, as illustrated for example in phantom lines in FIG. 3, then the hole 46 is blocked off and neither the liquid 12, nor the gas 14 can then flow out of the hole 46. Thus, it is apparent that the hole 46 should be near the first end 18 of the barrel 16.

Figure 2:
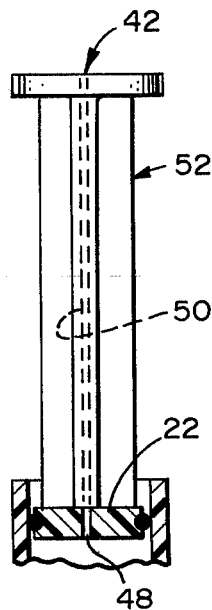
FIG. 2 illustrates an alternate embodiment of a portion of an improvement in accordance with the present invention.
Figure 4:
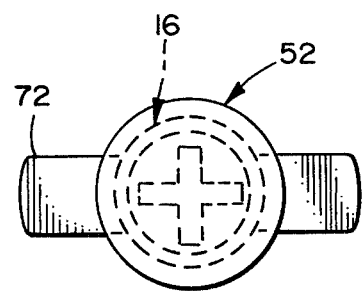
FIG. 4 illustrates a view taken along the line IV—IV of FIG. 3.

Referring now to FIG. 2, it will be noted that an alternate embodiment is shown therein of the means 42 for allowing the gas 14 to flow out of the barrel 16 above the liquid level 44 therein. In particular, FIG. 2 illustrates an embodiment wherein a hole 48 passes through the piston 22. As is further illustrated in FIG. 2, the hole 48 communicates with a passage 50 which itself proceeds through a handle 52 which extends axially from the piston 22 and out of the first end 18 of the barrel 16.

Adverting again to FIG. 1, the apparatus can also include a structure 54 which defines a controlled temperature chamber 56. In the particular embodiment illustrated, the structure 54 is simply a conventional constant temperature bath filled with a liquid 58, with the temperature of the bath being sensed by a temperature sensor 60. A temperature controller 62 causes a heater 64 to heat a heating element 66, and the liquid 58 is stirred in a conventional manner by a stirrer 68. It should be noted that the structure 54 is not limited to being a conventional bath filled with liquid but can be an air filled bath, can be a cavity in a block, for example a copper cavity, hinged at the side and having a bore to mate about the barrel 16, or can be any other structure 54 which will define a controlled temperature chamber 56. Temperature control can be accomplished outside of the chamber 56, if desired, and a controlled temperature fluid can then be flowed thereinto. This allows existing constant temperature baths to be used with the apparatus 10, thus potentially reducing expenditures for new equipment.

Figure 6:
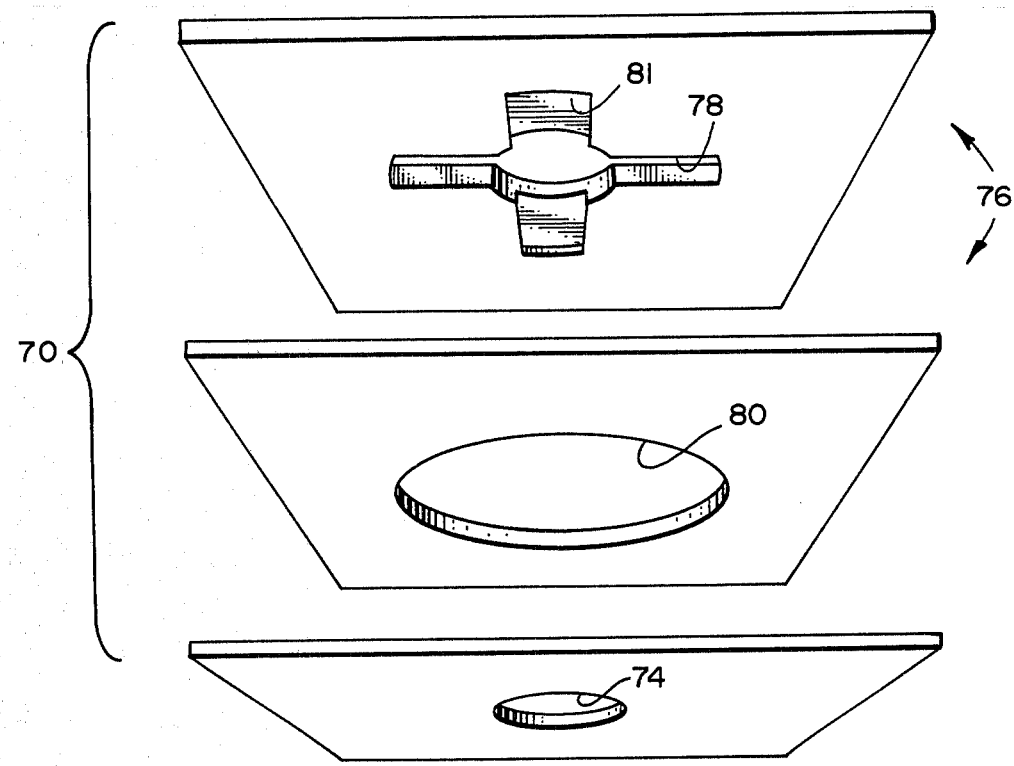
FIG. 6 illustrates, in exploded view, a detail in the structure shown in FIG. 1.

The apparatus can also include means 70 for removably mounting the barrel 16 with the second end 20 thereof in the chamber 56 up to at least about the liquid level 44. One particularly useful mounting means 70 is illustrated in FIGS. 1, 3 and 6. As may be seen in FIGS. 1, 3 and 6, the barrel 16 may include a non-circular flange 72 which extends laterally therefrom intermediate the first end 18 and the second end 20 thereof. In this embodiment, the barrel removably mounting means 70 includes a barrel excepting orifice 74 in the structure 54 of a size and shape sufficient to allow the second end 20 of the barrel 16 to extend therethrough and of a size and shape sufficient to prevent passage of the flange 72 therethrough.

The barrel removably mounting means 70 also includes means 76 for removably securing the flange 72 to the structure 54 adjacent the orifice 74 with the second end 20 of the barrel 16 projecting into the chamber 56. The particular flange securing means 76 illustrated in FIGS. 1 and 6 includes a flange accepting orifice 78, generally coaxial with the barrel accepting orifice 74. The flange accepting orifice 78 is of a size to allow the second end 20 of the barrel 16 and the flange 72 to pass therethrough. The flange accepting orifice 78 is shaped to allow the flange 72 to pass therethrough only when the flange 72 is particularly oriented with respect thereto. Thus, the flange 72 might be thought of as an ear extending downwardly from the barrel 16 and the flange accepting orifice 78 would be a matching or somewhat larger opening through which the ear could pass when properly aligned.

A locking orifice 80 is provided intermediate and generally coaxial with the barrel accepting orifice 74 and the flange accepting orifice 78. The locking orifice 80 is of a size and shape to accept the flange 72 in at least two orientations. The first of said orientations corresponds to the flange 72 being oriented to pass through the flange accepting orifice 78. The second orientation corresponds to the flange 72 being oriented to not pass through the flange accepting orifice 78.

One can insert the second end 20 of the barrel 16 downwardly first through the flange accepting orifice 78, then through the locking orifice 80, and then through the barrel accepting orifice 74. The flange 72 can be aligned to pass downwardly through the flange accepting orifice 78 and through the locking orifice 80. However, the flange 72 will not pass through the barrel accepting orifice 74, and hence, the flange 72 will abut the structure 54 atop the barrel accepting orifice 74. The barrel 16 is then rotated, causing the flange 72 to rotate so that the flange 72 is out of alignment with the flange accepting orifice 78. Thereby, the flange securing means 76 downwardly secures the flange 72 to the structure 54 adjacent the barrel accepting orifice 74 with the second end 20 of the barrel 16 projecting into the chamber 56. A recess 81 can be provided to accept the flange 72 and to keep it from rotating into an alignment where it is not locked atop the barrel accepting orifice 74.

Adverting again to FIG. 1, it is noted that the apparatus 10 may also include a source of the pressurized gas 14, such as a conventional gas cylinder 82. Gas 14 from the cylinder 82 will pass a conventional flow regulator 84 when a valve 86 is open and then will proceed via gas delivery means 88 to the flow control means 26. It will be noted that in the embodiment shown in FIG. 1, the chamber 56 also serves as means for adjusting the temperature of the gas 14, prior to its reaching the flow control means 26, to a desired value, generally the same temperature as the liquid 12. That is, a coiled tube 90 will generally sit within the chamber 56, wherein, through heat exchange with the liquid 58 therein, the gas 14 will be adjusted to the desired temperature. The tube 90 is of sufficient length to allow the second end 20 of the barrel 16 and the flow control means 26 to be removed from the chamber 56 while they are still secured together. This is important to the method of the invention as set out in more detail below.

Adverting briefly to FIG. 7, it will be seen that a cap 92 is provided having screw threads 94 which are adapted to be screwed onto the screw threads 38 adjacent the second end 20 of the barrel 16. The cap 92 serves a purpose which will become apparent from the description of the method which follows.

Referring to FIG. 3, it will be seen that the flow control means 26 has threads 96 on a lower end 98 thereof. The threads 96 mate with threads 100 on an adapter 102 which is attached to, and receives flow of the gas 14 from, the tube 90. Thus, the tube 90 is releasably secured to the flow control means 26. This allows the tube 90 to be disconnected from the flow control means 26. The barrel 16, with the flow control means 26 attached thereto and the piston 22 removed therefrom via the first end 18 thereof, can then have the liquid 12 added thereto. The flow control means 26 assures that the liquid 12 cannot escape from the second end 20 of the barrel 16. The piston 22 is then inserted to just above the hole 46 and the adapter 102 is connected to the flow control means 26.

METHOD

Utilizing an apparatus 10 in accordance with the present invention, a unique and advantageous method of equilibrating the gas 14 with the liquid 12 which fills the generally vertical barrel 16 up to the liquid level 44 therein, is disclosed. Briefly, with the barrel 16 being disposed generally vertically and with the liquid 12 inserted therein as explained above, the gas 14 is flowed upwardly into the second end 20 of the barrel 16 and through the liquid 12, with the second end 20 of the barrel 16 being originally the generally downwardly facing end thereof. At the same time, the liquid 12 is prevented from flowing downwardly out of the barrel 16 and more particularly out of the second end 20 thereof until a desired degree of equilibration of the gas 14 with the liquid 12 has been attained.

The flowing of the gas 14 is then halted while the preventing of the flow of the liquid 12 out of the second end 20 of the barrel 16 is continued. This can be accomplished by disconnecting the adapter 102 from the flow control means 26. The gas flow allowing means, that is the hole 46, or alternately the hole 48 and passage 50, is blocked off as by the operators finger or by inserting a plug (not illustrated). The barrel 16 is then inverted, thus making the originally generally downwardly facing second end 20 of the barrel 16 into a generally upwardly facing end thereof.

The flow preventing is stopped by removal of the flow control means 26 as by screwing it off of the second end 20 of the barrel 16. Since the barrel 16 is inverted, the liquid 12 is still retained within the barrel sitting atop the piston 22. The piston 22 is then advanced upwardly sufficiently to expel any remaining gas 14 from between the piston 22 and the second end 20 of the barrel 16. In the embodiment having the hole 46, the piston 22 travels upwardly past the hole 46, thus allowing the operator to remove his finger from the hole 46 if such is being used as a temporary stopper. The cap 92 is then screwed onto the second end 20 of the barrel 16 to cap it off. This assures that the composition of the liquid 12 within the barrel 16 is fixed. Through utilization of the controlled temperature chamber 56, the temperatures of the gas 12 and the liquid 14 are normally adjusted to a desired value prior to the flowing of the gas 14 through the liquid 12. The capped off barrel 16 is carried to a blood gas analyzer and the liquid 12 is used as a standard or as a test sample.

It will be apparent that a plurality of syringes 24 can br utilized with a single controlled temperature chamber 56 whereby as many samples as are desired can be prepared at a single time. Thus, the most expensive part of the overall combination, i.e., the temperature control part, does not need to be replicated for handling additional standard or test sample solutions. Further, the barrel 16 and the piston 22 can be made of relatively inexpensive materials, for example plastic, and can be manufactured by injection molding or another inexpensive molding technique. Thereby, operator time for cleaning the equilibration apparatus is eliminated, since the barrel 16 and piston 22 are simply thrown away and replaced with new parts for subsequent equilibrations.

INDUSTRIAL APPLICABILITY

The just described apparatus is particularly useful for preparing standards and samples for blood gas analysis. In such an apparatus, the liquid 12 might be water, a buffered aqueous solution, whole blood, or serum. However, the apparatus may also find use in other environments where it is desirable to equilibrate a gas with a liquid, and to be able to seal off the resulting liquid in a fast, inexpensive and straightforward manner.

Other aspects, objects and advantages of this invention can be ascertained from a study of the drawings, the disclosure and the appended claims.

I claim:

1. Apparatus for equilibrating a liquid sample with a gas, comprising:
    a barrel having openings at a first and at a second end thereof;

a piston in mating slidable relation within said barrel;

flow control means for allowing gas to flow upwardly through said opening in said second end of said barrel and for preventing flow of liquid out of said opening in said second end of said barrel; and means for allowing gas to flow out of said barrel above a liquid level therein.

2. Apparatus as in claim 1, including:
means for removably securing said flow control means to said second end of said barrel.

3. Apparatus as in claim 1, wherein said flow control means comprises a check valve.

4. Apparatus as in claim 1, wherein said flow control means comprises a membrane which is impervious to flow of said liquid sample and is pervious to flow of said gas.

5. Apparatus as in claim 1, wherein said gas flow allowing means comprises a hole through said barrel intermediate said liquid level and said first end of said barrel, said hole being positioned to allow said piston to move enough towards said first end of said barrel to allow gas to flow out of said hole.

6. Apparatus as in claim 5, wherein said hole is near said first end of said barrel.

7. Apparatus as in claim 1, wherein said gas flow allowing means comprises a hole through said piston.

8. Apparatus as in claim 1, including:
a handle attached to said piston and extending axially therefrom out of said first end of said barrel.

9. Apparatus as in claim 8, wherein said gas flow allowing means comprises a hole through said piston which communicates with a passage through said handle.

10. Apparatus as in claim 1, including:
a non-circular flange extending laterally from said barrel intermediate the first and second ends thereof.

11. Apparatus as in claim 1, including:
structure defining a controlled temperature chamber;
means for removably mounting said barrel with said second end thereof in said chamber up to about said liquid level.

12. Apparatus as in claim 11, including:
means for removably securing said flow control means to said second end of said barrel.

13. Apparatus as in claim 12, including:
a source of pressurized gas; and
means for delivering said pressurized gas to said flow control means.

14. Apparatus as in claim 13, including:
means for adjusting the temperature of said gas, prior to its reaching said flow control means, to a desired value.

15. Apparatus as in claim 14, wherein said gas temperature adjusting means comprises a tube positioned in said said chamber, said tube being of sufficient length to allow said second end of said barrel and said flow control means to be removed from said chamber while secured together.

16. Apparatus as in claim 11, including:
a non-circular flange extending laterally from said barrel intermediate said first and second ends thereof; and
wherein said barrel removably mounting means includes:
a barrel accepting orifice in said structure of a size and shape sufficient to allow said second end of said barrel to extend therethrough and to prevent passage of said flange therethrough; and means for removably securing said flange to said structure adjacent said orifice with said second end of said flange projecting into said chamber.

17. Apparatus as in claim 16, wherein said flange securing means includes:
a flange accepting orifice generally coaxial with said barrel accepting orifice, said flange accepting orifice being of a size to allow said second end of said barrel and said flange to pass therethrough, said flange accepting orifice being shaped to allow said flange to pass therethrough only when said flange is particularly oriented with respect thereto; and
a locking orifice intermediate and generally coaxial with said barrel and flange accepting orifices, said locking orifice being of a size and shape to accept said flange in at least two orientations, the first orientation corresponding to said flange being oriented to pass through said flange accepting orifice and the second orientation corresponding to said flange being oriented to not pass through said flange accepting orifice.

18. In a syringe apparatus which comprises a piston reciprocally matingly fitting within a barrel which has a downfacing end having an opening therethrough, an improvement comprising:
flow control means allowing a gas to flow upwardly through said opening into said downfacing end of said barrel and for preventing flow of a liquid downwardly through said opening in said end of said barrel; and
means for allowing said gas to flow out of said barrel above a level of said liquid held therein.

19. An apparatus as in claim 18, including:
means for removably securing said flow control means to said end of said barrel.

20. An apparatus as in claim 18, wherein said gas flow allowing means comprises a hole through said barrel intermediate said liquid level and an upfacing end of said barrel, said hole being positioned to allow said piston to move close enough to said upfacing end to allow said gas to flow out of said hole.

21. An apparatus as in claim 18, wherein said gas flow allowing means comprises a hole through said piston.

22. A method of equilibrating a gas with a liquid which fills a generally vertical barrel up to a liquid level therein, said barrel having a piston reciprocally matingly fitting therein and having means for allowing said gas to flow thereoutof above said liquid level therein, comprising:
flowing said gas upwardly through said liquid from an opening in an originally downwardly facing end of said barrel while preventing said liquid from flowing downwardly out of said opening in said barrel until a desired degree of equilibration has been attained;
halting said gas flowing while continuing said liquid flow preventing;
blocking off said gas flow allowing means;
inverting said barrel;
stopping said liquid flow preventing; and
advancing said piston sufficiently to expel any remaining gas from between said piston and said, originally generally downwardly facing and now generally upwardly facing, end of said barrel.

23. A method as in claim 22, including, following said piston advancing step:
capping off said now upwardly facing end of said barrel.

24. A method as in claim 22, including, prior to said gas flowing step:
adjusting the temperature of said gas and said liquid to desired values.

* * * * *